(12) United States Patent
Liu

(10) Patent No.: US 12,187,808 B2
(45) Date of Patent: Jan. 7, 2025

(54) GD2-BASED CHIMERIC ANTIGEN RECEPTOR AND APPLICATION THEREOF

(71) Applicant: Beijing Meikang Geno-Immune Biotechnology Co. Ltd., Beijing (CN)

(72) Inventor: Yu Chen Liu, Beijing (CN)

(73) Assignee: BEIJING MEIKANG GENO-IMMUNE BIOTECHNOLOGY CO. LTD., Beijing (CN)

(*) Notice: Subject to any disclaimer, the term of this patent is extended or adjusted under 35 U.S.C. 154(b) by 990 days.

(21) Appl. No.: 17/262,487

(22) PCT Filed: Jul. 24, 2019

(86) PCT No.: PCT/CN2019/097402
§ 371 (c)(1),
(2) Date: Jan. 22, 2021

(87) PCT Pub. No.: WO2020/020194
PCT Pub. Date: Jan. 30, 2020

(65) Prior Publication Data
US 2021/0309757 A1    Oct. 7, 2021

(30) Foreign Application Priority Data
Jul. 24, 2018 (CN) .......................... 201810821559.9

(51) Int. Cl.
*C07K 16/30* (2006.01)
*A61K 38/00* (2006.01)
(Continued)

(52) U.S. Cl.
CPC ...... *C07K 16/3084* (2013.01); *A61K 39/4611* (2023.05); *A61K 39/4631* (2023.05);
(Continued)

(58) Field of Classification Search
CPC combination set(s) only.
See application file for complete search history.

(56) References Cited

U.S. PATENT DOCUMENTS

2015/0140023 A1    5/2015  Birkle et al.

FOREIGN PATENT DOCUMENTS

| CN | 1726227 A | 1/2006 |
| CN | 105705165 A | 6/2016 |

(Continued)

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*

(Continued)

*Primary Examiner* — Adam Weidner
*Assistant Examiner* — Laura Ann Essex
(74) *Attorney, Agent, or Firm* — Gary J. Gershik

(57) ABSTRACT

The present application relates to a GD2-based chimeric antigen receptor comprising an antigen-binding domain, a transmembrane domain, a costimulatory signaling domain, a CD3ζ signaling domain, and a self-destructive domain in tandem arrangement; wherein the antigen-binding domain binds to a tumor surface antigen, wherein the tumor surface antigen is GD2, and the antigen-binding domain is a single-chain antibody against the tumor surface antigen GD2, wherein the self-destructive domain is a caspase 9 domain.

10 Claims, 3 Drawing Sheets

Specification includes a Sequence Listing.

(51) Int. Cl.
  *A61K 39/00* (2006.01)
  *A61P 35/00* (2006.01)
  *C07K 14/705* (2006.01)
  *C07K 14/725* (2006.01)
  *C12N 5/0783* (2010.01)
  *C12N 7/00* (2006.01)
  *C12N 9/64* (2006.01)
  *C12N 15/86* (2006.01)

(52) U.S. Cl.
  CPC ...... *A61K 39/464471* (2023.05); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *C12N 7/00* (2013.01); *C12N 9/6472* (2013.01); *C12N 15/86* (2013.01); *C12Y 304/22062* (2013.01); *A61K 38/00* (2013.01); *A61K 2039/505* (2013.01); *A61K 2239/31* (2023.05); *A61K 2239/38* (2023.05); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01); *C12N 2740/15021* (2013.01); *C12N 2740/15043* (2013.01)

(56) References Cited

FOREIGN PATENT DOCUMENTS

| CN | 106536563 | A |   | 3/2017 | |
| CN | 106749675 |   | * | 5/2017 | ............. A61K 35/17 |
| CN | 107106665 | A |   | 8/2017 | |
| CN | 107245107 | A |   | 10/2017 | |
| CN | 107312097 |   | * | 11/2017 | ......... A61K 39/0011 |
| CN | 108948211 | A |   | 12/2018 | |
| JP | 2007-537719 | A |   | 12/2007 | |
| JP | 2016-515519 | A |   | 5/2016 | |
| JP | 2016-520569 | A |   | 7/2016 | |
| JP | 2017-501212 | A |   | 1/2017 | |
| JP | 2017-508466 | A |   | 3/2017 | |
| WO | WO 2015/132604 | A1 |   | 9/2015 | |
| WO | WO-2016134284 | A1 | * | 8/2016 | ......... A61K 39/0011 |
| WO | WO 2016/187158 | A1 |   | 11/2016 | |
| WO | WO 2017/027291 | A1 |   | 2/2017 | |
| WO | WO 2020/020194 | A1 |   | 1/2020 | |

OTHER PUBLICATIONS

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
English translation of Junfang_CN107312097 (Year: 2017).*
Chang LJ, Liu X, He J. Lentiviral siRNAs targeting multiple highly conserved RNA sequences of human immunodeficiency virus type 1. Gene Ther. Jul. 2005; 12(14):1133-44. doi: 10.1038/sj.gt.3302509. Erratum in: Gene Ther. Aug. 2005;12(16):1289. PMID: 15750613. (Year: 2005).*
Debeb Bisrat, Zhang X, Krishnamurthy S, Gao H, Cohen E, Li L, Rodriguez AA, Landis MD, Lucci A, Ueno NT, Robertson F, Xu W, Lacerda L, Buchholz TA, Cristofanilli M, Reuben JM, Lewis MT, Woodward WA. Mol Cancer. Jul. 8, 2010;9:180. doi: 10.1186/1476-4598-9-180. PMID: 20615238; PMCID: PMC2915978. (Year: 2010).*
English Translation of Shenzhen_CN106749675 (Year: 2017).*
Gacerez AT, Arellano B, Sentman CL. How Chimeric Antigen Receptor Design Affects Adoptive T Cell Therapy. J Cell Physiol. Dec. 2016;231(12):2590-8. doi: 10.1002/jcp.25419. Epub Jun. 2, 2016. PMID: 27163336; PMCID: PMC4993661. (Year: 2016).*
Mar. 1, 2021 First Office Action issued in connection with Chinese Patent Application No. 201810821559.9.
Feb. 8, 2022 Japanese Office Action issued in connection with Japanese Patent Application No. JP 2021-503089 (including English language translation).
European Search Report issued Mar. 14, 2022 in connection with European Application No. 19 841 797. 4.
Coleman, J.E. et al., "Efficient large-scale production and concentration of HIV-1-based lentiviral vectors for use in vivo", Physiol Genomics, 2003, vol. 12, pp. 221-228.
Gargett, T. et al., "GD 2-specific CAR T Cells Undergo Potent Activation and Deletion Following Antigen Encounter but can be Protected From Activation-induced Cell Death by PD-1 Blockade", Molecular Therapy, 2016, vol. 24, No. 6, pp. 1135-1149.
Thomas, S. et al., "An Optimized GD 2-Targeting Retroviral Cassette for More Potent and Safer Cellular Therapy of Neuroblastoma and Other Cancers", PLOS One, 2016, vol. 11, pp. 1-19.
Yang, L. et al., "Chimeric Antigen Receptor 4SCAR-GD2-Modified T Cells Targeting High-Risk and Recurrent Neuroblastoma: A Phase II Multi-Center Trial in China", Blood, 2017, vol. 130, pp. 3335.
PCT International Patent Application Publication No. WO 16/187158 A1 (City of Hope) , published Nov. 24, 2016.
Chinese Patent Application No. CN 107106665 A, published on Aug. 29, 2017, (Memorial Sloan-Kettering Cancer Center AL.) ) (including English language translation of Abstract).
Chinese Patent Application No. CN 108948211 A, published on Dec. 7, 2018, (Beijing Meikang Jimian Biotechnology Co. Ltd.) (including English language translation of Abstract).
International Search Report issued by the International Searching Authority (ISA/O.E.P.M.) on Oct. 14, 2019 in connection with International Application No. PCT/CN2019/097402.

* cited by examiner

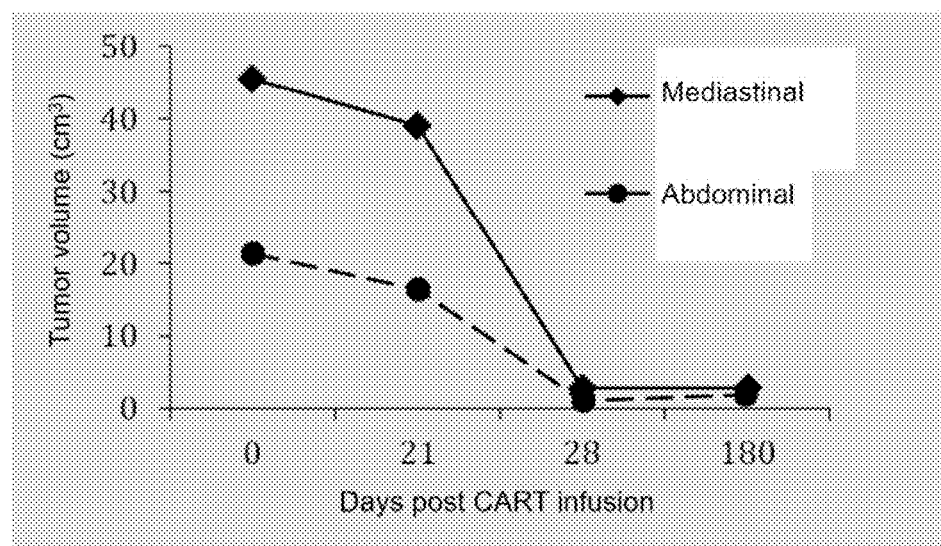
Figure 7
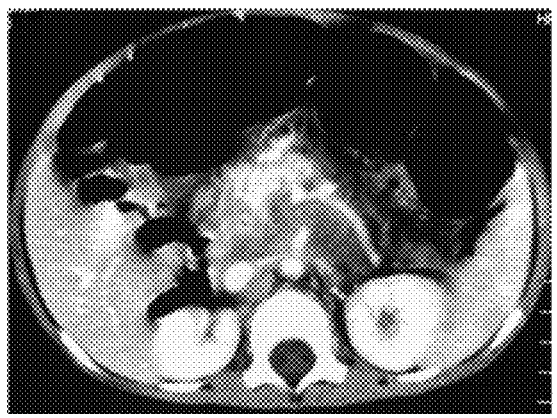 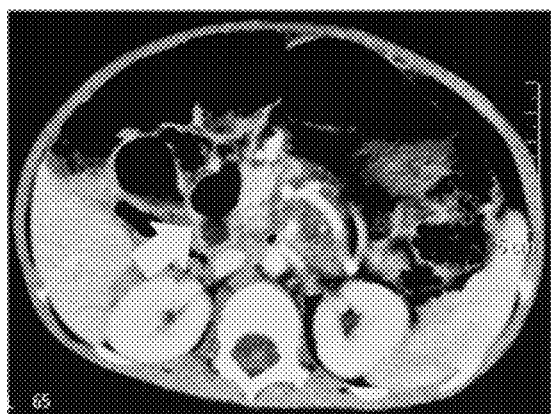
Figure 8(a)   Figure 8(b)

GD2-BASED CHIMERIC ANTIGEN RECEPTOR AND APPLICATION THEREOF

CROSS-REFERENCE TO RELATED APPLICATIONS

This application is a § 371 national stage of PCT International Application No. PCT/CN2019/097402, filed Jul. 24, 2019, claiming priority of Chinese Patent Application No. 201810821559.9, filed Jul. 24, 2018, the contents of each of which are hereby incorporated by reference into the application.

REFERENCE TO A SEQUENCE LISTING

This application incorporates-by-reference nucleotide and/or amino acid sequences which are present in the file named "210122_5886_91685_Sequence_Listing_SC.txt", which is 40 kilobytes in size, and which was created Jan. 22, 2021 in the IBM-PC machine format, having an operating system compatibility with MS-Windows, which is contained in the text file filed Jan. 22, 2021 as part of this application.

TECHNICAL FIELD

The present application relates to the field of cellular immunotherapy for tumors, especially to a GD2-based chimeric antigen receptor and application thereof, and in particular to a method for constructing a chimeric antigen receptor T (CAR-T) cell technology based on the tumor specific target GD2 and its application in anti-tumor therapy.

BACKGROUND

With the development of immunology theory and clinical technology for tumors, chimeric antigen receptor T cell (CAR-T) immunotherapy has become one of the most promising immunotherapies for cancer treatment. The chimeric antigen receptor (CAR) typically consists of a tumor-associated antigen-binding region, an extracellular hinge region, a transmembrane region, and an intracellular signaling region. The CAR generally comprises a single chain fragment variable (scFv) region of an antibody or a binding domain specific for a tumor-associated antigen (TAA), which is coupled to the cytoplasmic domain of a T cell signaling molecule via hinge and transmembrane regions. The most common lymphocyte activation moieties include a T cell costimulatory domain in tandem with a T-cell effector function triggering (e.g. CD3ζ) moiety. The CAR-mediated adoptive immunotherapy allows CAR-transplanted T cells to directly recognize the TAAs on target tumor cells in a non-HLA-restricted manner.

Neuroblastoma is the most common extracranial solid malignancy in children. Among them, 50% of the children are found to have large-scale spread and metastasis of tumors. Conventional surgery, chemotherapy, radiotherapy and autologous stem cell transplantation have limited therapeutic effects on this group of patients. Even when the condition is controlled to relieve, more than 80% of patients will relapse and die within one year. One approach to treat these patients is to genetically modify T cells to target the antigens expressed on tumor cells through the expression of CARs. CAR is an antigen receptor designed to recognize cell surface antigens in a human leukocyte antigen (HLA)-independent manner. Attempts in using genetically modified cells expressing CARs to treat these types of patients have achieved promising success.

GD2 is widely expressed in tumors such as neuroblastoma and melanoma, while its expression in normal tissues are low in amount and restricted. Therefore, GD2 is an ideal tumor antigen for immunotherapy. The therapy using an anti-GD2 antibody is a well-developed treatment in current immunotherapy for neuroblastoma and has achieved initial clinical success. However, the antibody therapy has the following limitations. The administered antibody exists in the peripheral blood, and is difficult to penetrate the tumor tissues or the sites with micro residual tumor. In addition, the administrated antibody is unable to persist in the body for a long time. In addition, the anti-GD2 antibody has a structure of a human-mouse chimeric antibody and thus may induce a resistance to the antibody, which increases the difficulty in retreatment.

CN 106536563 A disclosed a chimeric antigen receptor (CAR) comprising a disialoganglioside (GD2)-binding domain, wherein the GD2-binding domain comprises a) a heavy chain variable region (VH) having complementarity determining regions (CDRs) b) a light chain variable region (VL) having CDRs, and use of T cells expressing such CAR in the treatment of some cancers. The binding effect between the chimeric antigen receptor of this patent and GD2 needs to be improved, and the immune effector domains may further be improved.

In addition to the advantages of antibody therapy, fully humanized chimeric antigen receptor GD2-CART cells can accurately penetrate the tumor tissues and persist in the body for a long time due to the characteristics of the T cells themselves, and thus can provide a more effective treatment for relapsed and refractory neuroblastoma or other GD2-positive tumors.

SUMMARY

In view of the unsatisfactory targeting in treating tumors with CAR-T and the influence of tumor microenvironment on the therapeutic effects of CAR-T technology, the present application provides a GD2-based lentiviral chimeric antigen receptor and application thereof. The chimeric antigen receptor prepared in the present application increases the long-lasting immunity and safety of the CAR-T cells and enhances the therapeutic effects of CAR-T cells by genetically modifying the signaling domains of the GD2-CAR construct.

To achieve this purpose, the present application uses the following technical solutions:

In one aspect, the present application provides a GD2-based chimeric antigen receptor which comprises an antigen-binding domain, a transmembrane domain, a costimulatory signaling domain, a CD3ζ, signaling domain, and a self-destructive domain in tandem arrangement;

wherein the antigen-binding domain binds to a tumor surface antigen, wherein the tumor surface antigen is GD2, and the antigen-binding domain is a single-chain antibody against the tumor surface antigen GD2, wherein the single-chain antibody against the tumor surface antigen GD2 has an amino acid sequence selected from:
(a) the amino acid sequences as shown in SEQ ID No. 1-3; or
(b) amino acid sequences which are derived from the amino acid sequences as shown in SEQ ID No. 1-3 by substitution, addition and/or deletion of one or more amino acids, and bind specifically to the chimeric antigen receptor and have the function of binding to GD2 and inducing the T cell signaling.

In the present application, the gene structures of the single-chain antibody of the antigen-binding domain and the CAR are specifically modified, so that the genetically modified CAR-T cells are able to specifically bind to the GD antigen on tumors, which makes it possible to obtain relative moderate signal stimulation and exert an effective killing effect, while releasing the immune cytokine slowly, and thereby reducing the risk of the cytokine release syndrome. Compared with other chimeric antigen receptors and other tumor antigens, the CAR of the present application has a better effect and is safer.

The amino acid sequences (SEQ ID No. 1-3) of the single-chain antibody against the tumor surface antigen GD2 are listed as follows.

The amino acid sequence shown in SEQ ID NO. 1:

HPAFLLIPQVQLVESGPGVVQPGRSLRISCAVSGFSVTNYGVHWVRQPP

GKGLEWLGVIWAGGITNYNSAFMSRLTISKDNSKNTVYLQMNSLRAEDT

AMYYCASRGGHYGYALDYWGQGTLVTVSSGSTSGSGKPGSSEGSTKGEI

VMTQTPATLSVSAGERVTITCKASQSVSNDVTWYQQKPGQAPRLLIYSA

SNRYSGVPARFSGSGYGTEFTFTISSVQSEDFAVYFCQQDYSSFGQGTK

LEIK;

The amino acid sequence shown in SEQ ID NO. 2:

EVQLVQSGAEVEKPGASVKISCKASGSSFTGYNMNWVRQNIGKSLEWIG

AIDPYYGGTSYNQKFKGRATLTVDKSTSTAYMHLKSLRSEDTAVYYCVS

GMEYWGQGTSVTVSSGSTSGSGKPGSSEGSTKGDVVMTQTPLSLPVTPG

EPASISCRSSQSLVHRNGNTYLHWYLQKPGQSPKLLIHKVSNRFSGVPD

RFSGSGSGTDFTLKISRVEAEDLGVYFCSQSTHVPPLTFGAGTKLELK;

The amino acid sequence shown in SEQ ID NO. 3:

AFLLIPEVKLVESGGGLVLPGDSLRLSCATSEFTFTDYYMTWVRQPPRK

ALEWLGFIRNRANGYTTEYNPSVKGRFTISRDNSQSILYLQMNTLRTED

SATYYCARVSNWAFDYWGQGTTLTVSSGSTSGSGKPGSSEGSTKGDVVM

TQTPLSLPVSLGDQASISCRSSQSLLKNNGNTFLHWYLQKSGQSPKLLI

YKVSNRLSGVPDRFSGSGSGTYFTLKISRVEAEDLGVYFCSQSTHIPYT

FGGGTKLEIK.

In the present application, the signal structure of CAR against tumor surface antigen GD2 is specifically modified, and may also be rapidly modified by using alternative scFv genes of different anti-GD2 single-chain antibodies, such that the modified CAR exhibits a stronger immune-stimulating ability.

According to the present invention, the amino acid sequences which are derived from the amino acid sequences as shown in SEQ ID NOs. 1-3 by substitution, addition and/or deletion of one or more amino acids have at least 90% identity, preferably 95% identity with the amino acid sequences shown in SEQ ID NOs. 1-3. The modified amino acid sequences can still bind specifically to the chimeric antigen receptor and have the function of binding to GD2 and inducing the T cell signaling.

The 90% identity may be, for example, 90%, 91%, 92%, 93%, 94%, 95%, 96%, 97%, 98%, 99% or 100% identity.

According to the present application, the transmembrane domain is a CD28 transmembrane domain (CD28 extracellular and CD28 cell membrane signaling domains) and/or a CD8n transmembrane domain. In some particular embodiments, the transmembrane domain may be selected or modified by amino acid substitution.

According to the present application, the costimulatory signaling domain is the combination of a CD28 signaling domain and a 4-1BB intracellular signaling domain. The CD28 extracellular, cell membrane and intracellular signaling domains are combined into a full-length CD28 signaling domain. The arrangement of the full-length CD28 signaling domain and the 4-1BB signaling domain may be adjusted by those skilled in the art according to requirements. Different arrangements of the full-length CD28 signaling domain and the 4-1BB signaling domain will not affect the chimeric antigen receptor. An arrangement of CD28-4-1BB is used in the present application. The costimulatory signaling domain has the amino acid sequence as shown in SEQ ID NO. 4, which is specifically as follows:

IEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAP

PRDFAAYRSASGGGGSGGGGSVVKRGRKKLLYIFKQPFMRPVQTTQEED

GCSCRFPEEEEGGCEL.

The linker sequence therein is a repeated sequence of multiple GGGGS.

According to the present application, the full-length CD28 signaling domain comprises a CD28 extracellular signal, a CD28 cell membrane signal and a CD28 intracellular signal. The CD28 extracellular signal has the sequence as shown in SEQ ID NO. 5, which is specifically as follows: IEVMYPPPYLD-NEKSNGTIIHVKGKHLCPSPLFPGPSKP; the CD28 cell membrane signal has the sequence as shown in SEQ ID NO. 6, which is specifically as follows: FWVLVVVGGVLA-CYSLLVTVAFIIFWV; and the CD28 intracellular signal has the sequence as shown in SEQ ID NO. 7, which is specifically as follows: RSKRSRLLHSDYMNMT-PRRPGPTRKHYQPYAPPRDFAAYRSAS.

According to the present application, the 4-1BB intracellular signal has the sequence as shown in SEQ ID NO. 8, which is specifically as follows: VVKRGRKKLLY-IFKQPFMRPVQTTQEEDGCSCRFPEEEEGGCEL.

According to the present application, the self-destructable domain comprises an inducible caspase 9 domain. The inducible caspase 9 domain has the amino acid sequence as shown in SEQ ID NO.9, which is as follows:

GSGATNFSLLKQAGDVEENPGPMGVQVETISPGDGRTFPKRGQTCVVHY

TGMLEDGKKVDSSRDRNKPFKFMLGKQEVIRGWEEGVAQMSVGQRAKLT

ISPDYAYGATGHPGIIPPHATLVFDVELLKLEGGGGSGGGGSGAMVGAL

ESLRGNADLAYILSMEPCGHCLIINNVNFCRESGLRTRTGSNIDCEKLR

RRFSSLHFMVEVKGDLTAKKMVLALLELARQDHGALDCCVVVILSHGCQ

ASHLQFPGAVYGTDGCPVSVEKIVNIFNGTSCPSLGGKPKLFFIQACGG

EQKDHGFEVASTSPEDESPGSNPEPDATPFQEGLRTFDQLDAISSLPTP

SDIFVSYSTFPGFVSWRDPKSGSWYVETLDDIFEQWAHSEDLQSLLLRV

ANAVSVKGIYKQMPGCFNFLRKKLFFKTSAS.

According to the present application, the self-destructable domain is connected in tandem with the CD3ζ signaling domain via a 2A sequence. The 2A sequence will break the protein expressed by the self-destructable domain from the chimeric antigen receptor protein, thereby allowing the chimeric antigen receptor to exert its function. However, the self-destructable domain can be activated by injecting an activator, which induces cell death and makes the chimeric antigen receptor lose its function thereby.

According to the present application, the chimeric antigen receptor further comprises a signal peptide, which may be any signal peptide capable of directing the transmembrane transfer of the chimeric antigen receptor. A signal peptide conventional in the art may be selected by those skilled in the art according to requirements. The signal peptide is a Secretory signal peptide, which has the amino acid sequence as shown in SEQ ID NOs. 10-11. The Secretory signal peptide has the amino acid sequence (SEQ ID NO. 10) as follows: MLLLVTSLLLCELPHPAFLLIP; or the Secretory signal peptide has the amino acid sequence (SEQ ID NO. 11) as follows: MALPVTALLLPLALLLHAARP.

The chimeric antigen receptor of the present application may further comprise a hinge region. The hinge region may be selected by those skilled in the art according to actual situation, and is not particularly limited herein. The presence of a hinge region will not affect the performance of the chimeric antigen receptor of the present application.

The chimeric antigen receptor of the present application may further comprise a promoter, which may be EF1a or any one of the highly expressed promoters. It may be selected by those skilled in the art according to the actual situation, and is not particularly limited herein. The presence of a promoter will not affect the performance of the chimeric antigen receptor of the present application.

According to the present application, the chimeric antigen receptor comprises a signal peptide, an antigen-binding domain, a transmembrane domain, a costimulatory signaling domain, a CD3ζ signaling domain, a 2A sequence, and a self-destructable domain in tandem arrangement.

As a preferable technical solution, the chimeric antigen receptor is Secretory signal peptide, GD2 antigen-binding domain, CD8a and/or CD28 transmembrane domain, full-length CD28 signaling domain, 4-1BB intracellular signaling domain, CD3ζ signaling domain, 2A sequence and caspase 9 domain in tandem arrangement. Specifically, the arrangement is as follows:

Secretory-GD2scFv-CD28-4-1BB-CD3ζ-2A-FBKP.Casp9.

According to the present application, the chimeric antigen receptor Secretory-GD2 scFv-CD28-4-1BB-CD3ζ-2A-FBKP.Casp9 has the amino acid sequence as shown in SEQ ID NOs. 12-14, which are specifically listed as follows.

The amino acid sequence shown in SEQ ID NO. 12:

MLLLVTSLLLCELPHPAFLLIPQVQLVESGPGVVQPGRSLRISCAVSGF

SVTNYGVHWVRQPPGKGLEWLGVIWAGGITNYNSAFMSRLTISKDNSKN

TVYLQMNSLRAEDTAMYYCASRGGHYGYALDYWGQGTLVTVSSGSTSGS

GKPGSSEGSTKGEIVMTQTPATLSVSAGERVTITCKASQSVSNDVTWYQ

QKPGQAPRLLIYSASNRYSGVPARFSGSGYGTEFTFTISSVQSEDFAVY

FCQQDYSSFGQGTKLEIKAAAIEVMYPPPYLDNEKSNGTIIHVKGKHLC

PSPLFPGPSKPFWVLVVVGGVLACYSLLVTVAFIIFWVRSKRSRLLHSD

YMNMTPRRPGPTRKHYQPYAPPRDFAAYRSASGGGGSGGGGSVVKRGRK

KLLYIFKQPFMRPVQTTQEEDGCSCRFPEEEEGGCELGGGGSGGGGSGG

GGSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLST

ATKDTYDALHMQALPPRTSGSGATNFSLLKQAGDVEENPGPMGVQVETI

SPGDGRTFPKRGQTCVVHYTGMLEDGKKVDSSRDRNKPFKFMLGKQEVI

RGWEEGVAQMSVGQRAKLTISPDYAYGATGHPGIIPPHATLVFDVELLK

LEGGGGSGGGGSGAMVGALESLRGNADLAYILSMEPCGHCLIINNVNFC

RESGLRTRTGSNIDCEKLRRRFSSLHFMVEVKGDLTAKKMVLALLELAR

QDHGALDCCVVVILSHGCQASHLQFPGAVYGTDGCPVSVEKIVNIFNGT

SCPSLGGKPKLFFIQACGGEQKDHGFEVASTSPEDESPGSNPEPDATPF

QEGLRTFDQLDAISSLPTPSDIFVSYSTFPGFVSWRDPKSGSWYVETLD

DIFEQWAHSEDLQSLLLRVANAVSVKGIYKQMPGCFNFLRKKLFFKTSA

S;

The amino acid sequence shown in SEQ ID NO. 13:

MLLLVTSLLLCELPEVQLVQSGAEVEKPGASVKISCKASGSSFTGYNMN

WVRQNIGKSLEWIGAIDPYYGGTSYNQKFKGRATLTVDKSTSTAYMHLK

SLRSEDTAVYYCVSGMEYWGQGTSVTVSSGSTSGSGKPGSSEGSTKGDV

VMTQTPLSLPVTPGEPASISCRSSQSLVHRNGNTYLHWYLQKPGQSPKL

LIHKVSNRFSGVPDRFSGSGSGTDFTLKISRVEAEDLGVYFCSQSTHVP

PLTFGAGTKLELKAAAIEVMYPPPYLDNEKSNGTIIHVKGKHLCPSPLF

PGPSKPFWVLVVVGGVLACYSLLVTVAFIIFWVRSKRSRLLHSDYMNMT

PRRPGPTRKHYQPYAPPRDFAAYRSASGGGGSGGGGSVVKRGRKKLLYI

FKQPFMRPVQTTQEEDGCSCRFPEEEEGGCELGGGGSGGGGSGGGGSRV

KFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDT

YDALHMQALPPRTSGSGATNFSLLKQAGDVEENPGPMGVQVETISPGDG

RTFPKRGQTCVVHYTGMLEDGKKVDSSRDRNKPFKFMLGKQEVIRGWEE

GVAQMSVGQRAKLTISPDYAYGATGHPGIIPPHATLVFDVELLKLEGGG

GSGGGGSGAMVGALESLRGNADLAYILSMEPCGHCLIINNVNFCRESGL

RTRTGSNIDCEKLRRRFSSLHFMVEVKGDLTAKKMVLALLELARQDHGA

LDCCVVVILSHGCQASHLQFPGAVYGTDGCPVSVEKIVNIFNGTSCPSL

GGKPKLFFIQACGGEQKDHGFEVASTSPEDESPGSNPEPDATPFQEGLR

TFDQLDAISSLPTPSDIFVSYSTFPGFVSWRDPKSGSWYVETLDDIFEQ

WAHSEDLQSLLLRVANAVSVKGIYKQMPGCFNFLRKKLFFKTSAS;

The amino acid sequence shown in SEQ ID NO. 14:

MLLLVTSLLLCELPAFLLIPEVKLVESGGGLVLPGDSLRLSCATSEFTF

TDYYMTWVRQPPRKALEWLGFIRNRANGYTTEYNPSVKGRFTISRDNSQ

SILYLQMNTLRTEDSATYYCARVSNWAFDYWGQGTTLTVSSGSTSGSGK

PGSSEGSTKGDVVMTQTPLSLPVSLGDQASISCRSSQSLLKNNGNTFLH

WYLQKSGQSPKLLIYKVSNRLSGVPDRFSGSGSGTYFTLKISRVEAEDL

GVYFCSQSTHIPYTFGGGTKLEIKAAAIEVMYPPPYLDNEKSNGTIIHV

KGKHLCPSPLFPGPSKPFWVLVVVGGVLACYSLLVTVAFIIFWVRSKRS

RLLHSDYMNMTPRRPGPTRKHYQPYAPPRDFAAYRSASGGGGSGGGGSV

VKRGRKKLLYIFKQPFMRPVQTTQEEDGCSCRFPEEEEGGCELGGGGSG

GGGSGGGGSRVKFSRSADAPAYQQGQNQLYNELNLGRREEYDVLDKRRG

RDPEMGGKPRRKNPQEGLYNELQKDKMAEAYSEIGMKGERRRGKGHDGL

YQGLSTATKDTYDALHMQALPPRTSGSGATNFSLLKQAGDVEENPGPMG

VQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVF

DVELLKLEGGGGSGGGGSGAMVGALESLRGNADLAYILSMEPCGHCLII

NNVNFCRESGLRTRTGSNIDCEKLRRRFSSLHFMVEVKGDLTAKKMVLA

LLELARQDHGALDCCVVVILSHGCQASHLQFPGAVYGTDGCPVSVEKIV

NIFNGTSCPSLGGKPKLFFIQACGGEQKDHGFEVASTSPEDESPGSNPE

PDATPFQEGLRTFDQLDAISSLPTPSDIFVSYSTFPGFVSWRDPKSGSW

YVETLDDIFEQWAHSEDLQSLLLRVANAVSVKGIYKQMPGCFNFLRKKL

FFKTSAS.

In a second aspect, the present application provides a viral vector comprising the chimeric antigen receptor as described in the first aspect.

According to the present application, the viral vector is a lentiviral vector and/or a retroviral vector, preferably a lentiviral vector.

In a third aspect, the present application provides a T cell which is virally transduced with a nucleic acid sequence encoding the chimeric antigen receptor as described in the first aspect for expression.

According to the present application, the T cell is transduced via a viral vector and/or a eukaryotic expression plasmid, preferably via a viral vector.

In the present application, the T cell has a good targeted killing effect and is capable of releasing low dose of immune factors, and has a property of low-toxicity and high-immunity killing response.

In a fourth aspect, the present application provides a recombinant lentivirus which is obtained by co-transfecting a mammalian cell with the viral vector as described in the first aspect and packaging helper plasmids pNHP and pHEF-VSVG.

According to the present application, the mammalian cell is any one of the group consisting of a 293 cell, a 293T cell and a TE671 cell, or a combination of at least two thereof.

In a fifth aspect, the present application provides a composition comprising the chimeric antigen receptor as described in the first aspect and/or the recombinant lentivirus as described in the fourth aspect.

In a sixth aspect, the present application provides use of the chimeric antigen receptor as described in the first aspect, the viral vector as described in the second aspect, the T cell as described in the third aspect, the recombinant lentivirus as described in the fourth aspect or the composition as described in the fifth aspect for the preparation of chimeric antigen receptor T cells and tumor therapeutic drugs.

Preferably, the tumor is a tumor disease in which the GD2 antigen is specifically expressed, and the tumor disease in which the GD2 antigen is specifically expressed is neuroblastoma.

Compared with the prior art, the present application has the following beneficial effects:

(1) In the present application, the T cell intracellular costimulatory signaling domain of the chimeric antigen receptor against the tumor surface antigen GD2 is specifically genetically modified. The modified chimeric antigen receptor produces a better response effect after specifically binding to GD2, such that the CAR-T cells produce a stronger immune response to tumors;

(2) When the present application is actually administrated to the human body, the CAR-T cells of the present application show higher safety comparing with other GD2-based chimeric antigen receptor T cells. Even if an adverse reaction occurs, the CAR-T cells of the present application may also be removed by a drug that induces apoptosis because they contain a signal that induces apoptosis.

(3) After the reinfusion of the CAR-T cells of the present application, the presence of CAR-T in vivo can be detected for a long time, which can prove its long-lasting effect and provide a long-term remission to the patients.

BRIEF DESCRIPTION OF DRAWINGS

FIG. 4 is a diagram showing the immunohistochemical staining results of tumor sections from a patient with neuroblastoma, wherein

FIG. 7 is a graph showing the curve of the changes in tumor volume detected by B-scan ultrasonography in a patient with neuroblastoma post the GD2-CART reinfusion;

FIG. 8 is a graph showing the abdominal mass detected by enhanced CT in a patient with neuroblastoma before (FIG. 8(a)) and post (FIG. 8(b)) the GD2-CART reinfusion.

DETAILED DESCRIPTION

In order to further illustrate the technical measures adopted by the present application and the effects thereof, the technical solutions of the present application are further described below with reference to the accompanying drawings and specific embodiments, and however, the present application is not limited to the scope of the embodiments.

In the examples, techniques or conditions, which are not specifically indicated, are performed according to techniques or conditions described in the literature of the art, or according to product instructions. The reagents or instruments for use, which are not indicated with manufacturers, are conventional products that are commercially available from many sources.

Example 1: Construction of a Chimeric Antigen Receptor (I)

Figure 1:
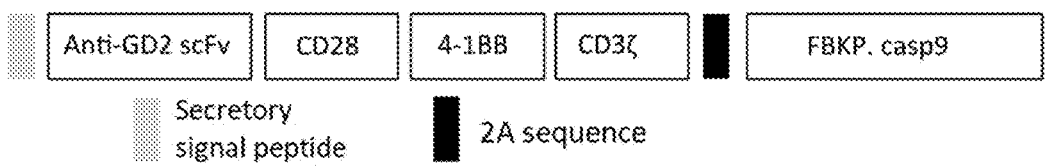
FIG. 1 is a diagram showing the synthetic gene sequence map of the chimeric antigen receptor of the present application.

(1) The Secretory signal peptide, GD2 antigen-binding domain, CD28 extracellular and transmembrane domains, CD28 intracellular signaling domain and 4-1BB signaling domain, CD3ζ signaling domain, 2A sequence and caspase 9 domain as shown in FIG. 1, i.e., Secretory-GD2scFv-CD28-4-1BB-CD3ζ-2A-FBKP.Casp9 was synthesized by whole gene synthesis.

The amino acid sequence (SEQ ID NO. 12) of the chimeric antigen receptor was as follows:

MLLLVTSLLLCELPHPAFLLIPQVQLVESGPGVVQPGRSLRISCAVSGF

SVTNYGVHWVRQPPGKGLEWLGVIWAGGITNYNSAFMSRLTISKDNSKN

TVYLQMNSLRAEDTAMYYCASRGGHYGYALDYWGQGTLVTVSSGSTSGS

GKPGSSEGSTKGEIVMTQTPATLSVSAGERVTITCKASQSVSNDVTWYQ

QKPGQAPRLLIYSASNRYSGVPARFSGSGYGTEFTFTISSVQSEDFAVY

FCQQDYSSFGQGTKLEIKAAAIEVMYPPPYLDNEKSNGTIIHVKGKHLC

PSPLFPGPSKPFWVLVVVGGVLACYSLLVTVAFIIFWVRSKRSRLLHSD

YMNMTPRRPGPTRKHYQPYAPPRDFAAYRSASGGGGSGGGGSVVKRGRK

KLLYIFKQPFMRPVQTTQEEDGCSCRFPEEEEGGCELGGGGSGGGGSGG

GGSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLST

ATKDTYDALHMQALPPRTSGSGATNFSLLKQAGDVEENPGPMGVQVETI

SPGDGRTFPKRGQTCVVHYTGMLEDGKKVDSSRDRNKPFKFMLGKQEVI

RGWEEGVAQMSVGQRAKLTISPDYAYGATGHPGIIPPHATLVFDVELLK

LEGGGGSGGGGSGAMVGALESLRGNADLAYILSMEPCGHCLIINNVNFC

RESGLRTRTGSNIDCEKLRRRFSSLHFMVEVKGDLTAKKMVLALLELAR

QDHGALDCCVVVILSHGCQASHLQFPGAVYGTDGCPVSVEKIVNIFNGT

SCPSLGGKPKLFFIQACGGEQKDHGFEVASTSPEDESPGSNPEPDATPF

QEGLRTFDQLDAISSLPTPSDIFVSYSTFPGFVSWRDPKSGSWYVETLD

DIFEQWAHSEDLQSLLLRVANAVSVKGIYKQMPGCFNFLRKKLFFKTSA

S.

Example 2: Construction of a Chimeric Antigen Receptor (II)

(1) The Secretory signal peptide, GD2 antigen-binding domain, CD28 extracellular and transmembrane domains, CD28 signaling domain and 4-1BB signaling domain, CD3ζ signaling domain, 2A sequence and Caspase 9 domain, i.e., Secretory-GD2scFv-CD28-4-1BB-CD3ζ-2A-FBKP.Casp9 was synthesized by whole gene synthesis.

The amino acid sequence (SEQ ID NO. 13) of the chimeric antigen receptor was as follows:

MLLLVTSLLLCELPEVQLVQSGAEVEKPGASVKISCKASGSSFTGYNMN

WVRQNIGKSLEWIGAIDPYYGGTSYNQKFKGRATLTVDKSTSTAYMHLK

SLRSEDTAVYYCVSGMEYWGQGTSVTVSSGSTSGSGKPGSSEGSTKGDV

VMTQTPLSLPVTPGEPASISCRSSQSLVHRNGNTYLHWYLQKPGQSPKL

LIHKVSNRFSGVPDRFSGSGSGTDFTLKISRVEAEDLGVYFCSQSTHVP

PLTFGAGTKLELKAAAIEVMYPPPYLDNEKSNGTIIHVKGKHLCPSPLF

PGPSKPFWVLVVVGGVLACYSLLVTVAFIIFWVRSKRSRLLHSDYMNMT

PRRPGPTRKHYQPYAPPRDFAAYRSASGGGGSGGGGSVVKRGRKKLLYI

FKQPFMRPVQTTQEEDGCSCRFPEEEEGGCELGGGGSGGGGSGGGGSRV

KFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDT

YDALHMQALPPRTSGSGATNFSLLKQAGDVEENPGPMGVQVETISPGDG

RTFPKRGQTCVVHYTGMLEDGKKVDSSRDRNKPFKFMLGKQEVIRGWEE

GVAQMSVGQRAKLTISPDYAYGATGHPGIIPPHATLVFDVELLKLEGGG

GSGGGGSGAMVGALESLRGNADLAYILSMEPCGHCLIINNVNFCRESGL

RTRTGSNIDCEKLRRRFSSLHFMVEVKGDLTAKKMVLALLELARQDHGA

LDCCVVVILSHGCQASHLQFPGAVYGTDGCPVSVEKIVNIFNGTSCPSL

GGKPKLFFIQACGGEQKDHGFEVASTSPEDESPGSNPEPDATPFQEGLR

TFDQLDAISSLPTPSDIFVSYSTFPGFVSWRDPKSGSWYVETLDDIFEQ

WAHSEDLQSLLLRVANAVSVKGIYKQMPGCFNFLRKKLFFKTSAS.

Example 3: Construction of a Chimeric Antigen Receptor (III)

(1) The Secretory signal peptide, GD2 antigen-binding domain, CD28 extracellular and transmembrane domains, CD28 signaling domain and 4-1BB signaling domain, CD3ζ signaling domain, 2A sequence and Caspase 9 domain, i.e., Secretory-GD2scFv-CD28-4-1BB-CD3ζ-2A-FBKP.Casp9 was synthesized by whole gene synthesis.

The amino acid sequence (SEQ ID NO. 14) of the chimeric antigen receptor was as follows:

MLLLVTSLLLCELPAFLLIPEVKLVESGGGLVLPGDSLRLSCATSEFTF

TDYYMTWVRQPPRKALEWLGFIRNRANGYTTEYNPSVKGRFTISRDNSQ

SILYLQMNTLRTEDSATYYCARVSNWAFDYWGQGTTLTVSSGSTSGSGK

PGSSEGSTKGDVVMTQTPLSLPVSLGDQASISCRSSQSLLKNNGNTFLH

WYLQKSGQSPKLLIYKVSNRLSGVPDRFSGSGSGTYFTLKISRVEAEDL

GVYFCSQSTHIPYTFGGGTKLEIKAAAIEVMYPPPYLDNEKSNGTIIHV

KGKHLCPSPLFPGPSKPFWVLVVVGGVLACYSLLVTVAFIIFWVRSKRS

RLLHSDYMNMTPRRPGPTRKHYQPYAPPRDFAAYRSASGGGGSGGGGSV

-continued
VKRGRKKLLYIFKQPFMRPVQTTQEEDGCSCRFPEEEEGGCELGGGGSG

GGGSGGGGSRVKFSRSADAPAYQQGQNQLYNELNLGRREEYDVLDKRRG

RDPEMGGKPRRKNPQEGLYNELQKDKMAEAYSEIGMKGERRRGKGHDGL

YQGLSTATKDTYDALHMQALPPRTSGSGATNFSLLKQAGDVEENPGPMG

VQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVF

DVELLKLEGGGGSGGGGSGAMVGALESLRGNADLAYILSMEPCGHCLII

NNVNFCRESGLRTRTGSNIDCEKLRRRFSSLHFMVEVKGDLTAKKMVLA

LLELARQDHGALDCCVVVILSHGCQASHLQFPGAVYGTDGCPVSVEKIV

NIFNGTSCPSLGGKPKLFFIQACGGEQKDHGFEVASTSPEDESPGSNPE

PDATPFQEGLRTFDQLDAISSLPTPSDIFVSYSTFPGFVSWRDPKSGSW

YVETLDDIFEQWAHSEDLQSLLLRVANAVSVKGIYKQMPGCFNFLRKKL

FFKTSAS.

Example 4: Lentiviral Packaging (1) 293T cells can be cultured in a six-well plate at a density of $1 \times 10^6$ cells/well for 17-18 hours;

(2) 600 µL/well of fresh DMEM containing 10% FBS was added;

(3) To a sterile centrifuge tube were added the following reagents: 75 µL of DMEM collected from each well, helper DNA mix (pNHP, pHEF-VSV-G), a GFP reporter plasmid, and the pTYF CAR DNA vector (from Example 1, 2 or 3), and then vortexed;

(4) 7 µL of Superfect was taken from the center of each well, added to the centrifuge tube, mixed by pipetting up and down for five times, and allowed to stand at room temperature for 7-10 minutes;

(5) To each culture well the DNA-Superfect mixture in the centrifuge tube was added dropwise, mixed by vortex;

(6) Incubated in an incubator at 37° C. with 3% $CO_2$ for 4-5 hours;

(7) The media was removed, the cells were rinsed with 1.5 mL of culture media, and then 1.5 mL of media was added for further incubation:

(8) The plate was placed back into the incubator with 5% $CO_2$ for overnight incubation. The next morning, transfection efficiency was observed based on GFP expression with a fluorescence microscope.

Example 5: Lentivirus Purification and Concentration

1) Virus Purification

Cell debris were removed by a centrifugation at 1000 g for 5 minutes to obtain virus supernatant. The virus supernatant was filtered with a low protein-binding filter, and then the virus was divided into small portions and stored at −80° C.;

Typically, lentiviral vectors at a titer of $10^6$ to $10^8$ transducing units can be produced by transfected cells per ml media.

2) Concentration of Lentivirus with a Filter (1) In a biosafety cabinet, a filter tube was disinfected with alcohol and then washed with sterile PBS;

(2) virus supernatant was added to the filter tube, then centrifuged at 2500 g for 30 minutes or until the virus volume was reduced by 20-50 times;

(3) The filter tube was shaken, then centrifuged at 400 g for 2 minutes, and the concentrated virus was collected into a collection cup, and finally the virus in all the tubes was collected into one centrifuge tube.

Example 6: Transduction of CAR-T Cells

The activated T cells were inoculated with AIM-V media containing growth factors IL-2, IL-7 and IL-15, and 10 µg/mL of polybrene was added. The concentrated lentivirus comprising CAR gene was added, centrifuged at a centrifugal force of 100 g at room temperature for 100 minutes, then incubated at 37° C. for 24 hours. Culture media was then added and incubated for 4 days. Then the cells were harvested and counted, and cultured for 2 days before infusion to patients.

Figure 2:
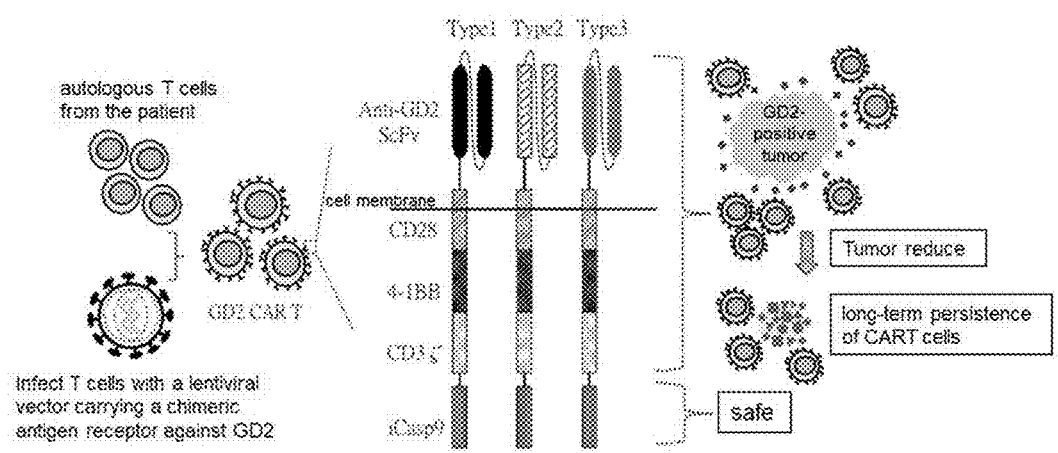
FIG. 2 is a diagram showing an application of safe and effective lentiviral CAR vectors, wherein Type 1 is the chimeric antigen receptor prepared in Example 1, Type 2 is the chimeric antigen receptor prepared in Example 2, and Type 3 is the chimeric antigen receptor prepared in Example 3.

The effects on treating tumors as shown in FIG. 2 which indicated that the CAR-T cells effectively reduced the tumor, and it was safe. The effects were specifically verified by in vitro and in vivo assays.

Figure 3:
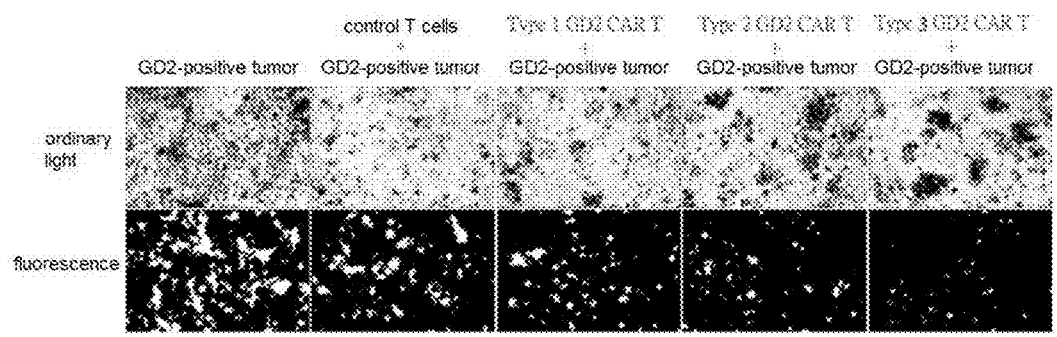
FIG. 3 is a diagram showing the in vitro killing results of three types of GD2ScFv CAR T cells, wherein Type 1 is the chimeric antigen receptor prepared in Example 1, Type 2 is the chimeric antigen receptor prepared in Example 2, and Type 3 is the chimeric antigen receptor prepared in Example 3.

Example 7: In Vitro Killing Assay with CAR-T Cells (1) A GD2-positive tumor cell line was transduced with lentiviral vectors expressing a green fluorescent protein (GFP) and the GFP was stably expressed;

(2) Non-specific T cells or CAR-T cells different from the GD2 scFv were co-cultured with said tumor cells in an incubator at 37° C., 5% $CO_2$ for 24-72 h;

(3) The survival of tumor cells was observed by fluorescence microscopy. The in vitro killing efficiency of different GD2-CAR-T cells were evaluated based on the fact that dead tumor cells did not express green fluorescent protein. The results were shown in FIG. 3;

It can be seen from FIG. 3 that compared with the control T cells, the three types of ScFv GD2-CAR-T cells had obvious killing effects, wherein the Type 3 scFv showed the best effect, thus confirming that the vector material used in the present application quickly screened out effective CAR structures for subsequent clinical use.

Figures 4A, 4B:
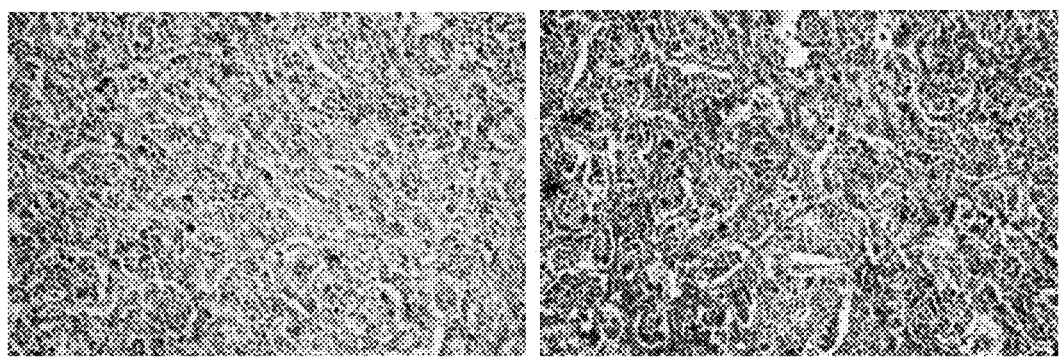
FIG. 4(a) is a negative control of the tumor section.
FIG. 4(b) shows positive GD2 expression.

Example 8: Therapeutic Effects of the CAR-T Cells (1) The unstained tumor sections from patients with neuroblastoma were confirmed for positive GD2 expression by immunohistochemical staining. The results were as shown in FIG. 4. Tumors with high GD2 expression can be distinguished between FIG. 4(a) and FIG. 4(b).

(2) White blood cells were collected from patients. Peripheral mononuclear lymphocytes were separated from the white blood cells by gradient density centrifugation with Ficoll and T cells were screened with CD3 magnetic beads. Anti-CD28 antibody was added into the T cells for T cell activation. The subsequent GD2-CART preparation was carried out at $1 \times 10^6$ CART cells/kg body weight;

(3) Patients were pretreated with low-dose chemotherapy. The pretreatment regimen was administration of cyclophosphamide 250 mg/m$^2$ for 3 days and fludarabine 25 mg/m$^2$ for 3 days. The pretreatment was performed at 24 h before CART infusion and lasted for 3 days (the chemotherapy regimen can be modified according to the patient's condition and this example is only used as an enumeration);

(4) CAR T cells were reinfused via intravenous injection.

(5) After the infusion, the patients were monitored and evaluated for toxic response by the clinician. The results were shown in FIG. 5.

Figure 5:
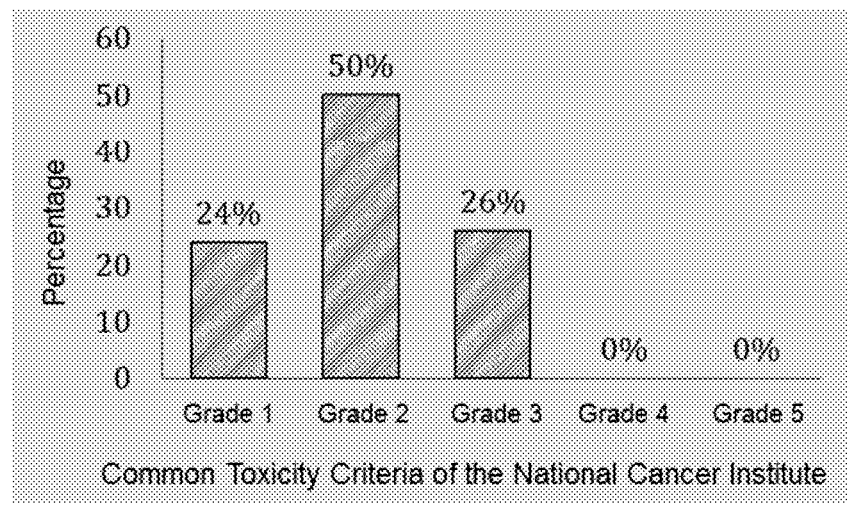
FIG. 5 is a graph showing the toxicity in patients with neuroblastoma post the GD2-CART reinfusion.

The safety of the GD2-CAR T cells can be seen from the statistical results in FIG. 5, the GD2-CAR T cells were safe. After the infusion, 24% of patients had no adverse reactions, 50% had Grade 1 adverse reactions, and 26% had Grade 2 adverse reactions. Those adverse reactions included fever, fatigue, rash and hypotension, etc., which can be effectively controlled in clinical.

(6) After the infusion, a small amount of peripheral blood was obtained from the patients, and the peripheral mononuclear lymphocytes were prepared for chromosomal DNA (gDNA) extraction. The CAR copy number in the peripheral blood was quantified by qPCR using specific primers. The results are shown in FIG. 6.

Figure 6:
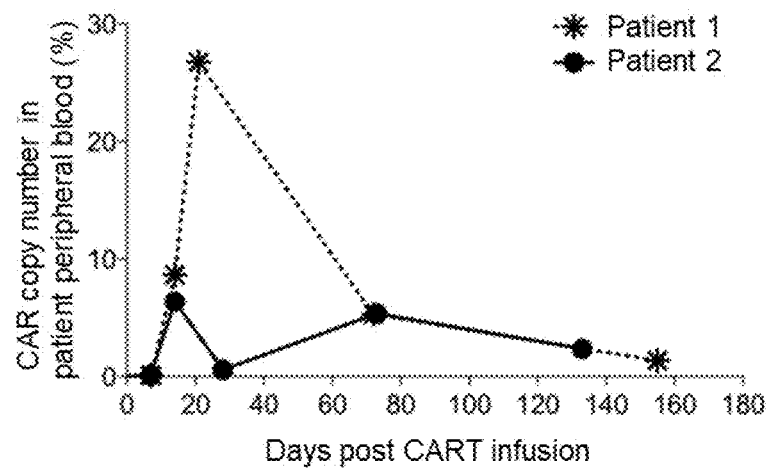
FIG. 6 is a graph showing the curve of the in vivo CAR copy number post the GD2-CART reinfusion.

As can be seen from FIG. 6, the CAR value in vivo peaked in the patient about 20 days after infusion, and maintained in the body for about half a year.

(7) The tumor size was evaluated by imaging after GD2-CART infusion, and the results were shown in FIG. 7 and FIG. 8.

As can be seen from FIG. 7, at 28 days after GD2-CART infusion, the abdominal and mediastinal masses in the patient as detected by B-scan ultrasonography was reduced by about 95% compared with that before infusion, and maintained for half a year. So far, the patient's condition is still stable. As can be seen from FIG. 8(a)-FIG. 8(b), the abdominal mass in another patient was scanned with enhanced CT two months after infusion, and the mass was reduced from the original size of 1.9 cm in length and 4.9 cm in width as shown in FIG. 8(a) to the size of 1.9 cm in length and 3.2 cm in width as shown in FIG. 8(b).

In summary, the GD2-CAR T cells of the present application had a better effect than other chimeric antigen receptors and other tumor antigens, and had safety and a long-lasting effect, and did achieve a good effect in patients with relapsed and refractory stage IV neuroblastoma.

The Applicant declares that detailed methods of the present application have been described through the above examples, and however, the present application is not limited to the above detailed methods. That is to say, it does not mean that the implementation of the present application must rely on the above detailed methods. Those skilled in the art should understand that any improvement on the present application, including the equivalent replacement of the raw materials or the addition of auxiliary components to the product of the present application, and the selection of specific methods, etc., falls within the protection scope and the disclosure scope of the present application.

The invention claimed is:

1. A chimeric antigen receptor, wherein
the chimeric antigen receptor comprises a Secretory signal peptide, GD2 antigen-binding domain, CD8α and/or CD28 transmembrane domain, CD28 signaling domain, 4-1BB signaling domain, CD3ζ signaling domain, 2A sequence, and caspase 9 domain in tandem arrangement;
the chimeric antigen receptor is Secretory-GD2-CD28-4-1BB-CD3ζ-2A-FBKP.Casp9; and
the chimeric antigen receptor Secretory-GD2-CD28-4-1BB-CD3ζ-2A-FBKP.Casp9 comprises the amino acid sequence as shown in SEQ ID NOs: 13-14.

2. A viral vector encoding the chimeric antigen receptor according to claim 1.

3. The viral vector according to claim 2, wherein the viral vector is a lentiviral vector and/or a retroviral vector.

4. A method of obtaining recombinant lentivirus, comprising co-transfection of a mammalian cell with the viral vector according to claim 2 and packaging helper plasmids pNHP and pHEF-VSVG.

5. The method according to claim 4, wherein the mammalian cell is selected from the group consisting of a 293 cell, a 293T cell, a TE671 cell, and the combination thereof.

6. A T cell which is transfected with a nucleic acid sequence encoding the chimeric antigen receptor according to claim 1 for expression.

7. The T cell according to claim 6, wherein the T cell is transfected via a viral vector and/or a eukaryotic expression plasmid.

8. A method for treating a tumor, comprising administrating to a patient in need thereof an effective amount of chimeric antigen receptor T cells or immune cells or tumor therapeutics comprising the chimeric antigen receptor according to claim 1.

9. The method according to claim 8, wherein the tumor is a cancer in which the GD2 antigen is specifically expressed.

10. The method according to claim 9, wherein the tumor in which the GD2 antigen is specifically expressed is neuroblastoma.

* * * * *

SEQUENCE LISTING

```
<160> NUMBER OF SEQ ID NOS: 14

<210> SEQ ID NO 1
<211> LENGTH: 249
<212> TYPE: PRT
<213> ORGANISM: Artificial sequence
<220> FEATURE:
<223> OTHER INFORMATION: anti-GD2 single-chain antibody

<400> SEQUENCE: 1

His Pro Ala Phe Leu Leu Ile Pro Gln Val Gln Leu Val Glu Ser Gly
1               5                   10                  15

Pro Gly Val Val Gln Pro Gly Arg Ser Leu Arg Ile Ser Cys Ala Val
            20                  25                  30

Ser Gly Phe Ser Val Thr Asn Tyr Gly Val His Trp Val Arg Gln Pro
        35                  40                  45

Pro Gly Lys Gly Leu Glu Trp Leu Gly Val Ile Trp Ala Gly Gly Ile
    50                  55                  60

Thr Asn Tyr Asn Ser Ala Phe Met Ser Arg Leu Thr Ile Ser Lys Asp
65                  70                  75                  80

Asn Ser Lys Asn Thr Val Tyr Leu Gln Met Asn Ser Leu Arg Ala Glu
                85                  90                  95

Asp Thr Ala Met Tyr Tyr Cys Ala Ser Arg Gly Gly His Tyr Gly Tyr
            100                 105                 110

Ala Leu Asp Tyr Trp Gly Gln Gly Thr Leu Val Thr Val Ser Ser Gly
        115                 120                 125

Ser Thr Ser Gly Ser Gly Lys Pro Gly Ser Ser Glu Gly Ser Thr Lys
    130                 135                 140

Gly Glu Ile Val Met Thr Gln Thr Pro Ala Thr Leu Ser Val Ser Ala
145                 150                 155                 160

Gly Glu Arg Val Thr Ile Thr Cys Lys Ala Ser Gln Ser Val Ser Asn
                165                 170                 175

Asp Val Thr Trp Tyr Gln Gln Lys Pro Gly Gln Ala Pro Arg Leu Leu
            180                 185                 190
```

Ile Tyr Ser Ala Ser Asn Arg Tyr Ser Gly Val Pro Ala Arg Phe Ser
            195                 200                 205

Gly Ser Gly Tyr Gly Thr Glu Phe Thr Phe Thr Ile Ser Ser Val Gln
210                 215                 220

Ser Glu Asp Phe Ala Val Tyr Phe Cys Gln Gln Asp Tyr Ser Ser Phe
225                 230                 235                 240

Gly Gln Gly Thr Lys Leu Glu Ile Lys
            245

<210> SEQ ID NO 2
<211> LENGTH: 244
<212> TYPE: PRT
<213> ORGANISM: Artificial sequence
<220> FEATURE:
<223> OTHER INFORMATION: anti-GD2 single-chain antibody

<400> SEQUENCE: 2

Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
            100                 105                 110

Ser Gly Ser Thr Ser Gly Ser Gly Lys Pro Gly Ser Gly Glu Gly Ser
        115                 120                 125

Thr Lys Gly Asp Val Val Met Thr Gln Thr Pro Leu Ser Leu Pro Val
130                 135                 140

Thr Pro Gly Glu Pro Ala Ser Ile Ser Cys Arg Ser Ser Gln Ser Leu
145                 150                 155                 160

Val His Arg Asn Gly Asn Thr Tyr Leu His Trp Tyr Leu Gln Lys Pro
                165                 170                 175

Gly Gln Ser Pro Lys Leu Leu Ile His Lys Val Ser Asn Arg Phe Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Leu Gly Val Tyr Phe Cys
    210                 215                 220

Ser Gln Ser Thr His Val Pro Pro Leu Thr Phe Gly Ala Gly Thr Lys
225                 230                 235                 240

Leu Glu Leu Lys

<210> SEQ ID NO 3
<211> LENGTH: 255
<212> TYPE: PRT
<213> ORGANISM: Artificial sequence
<220> FEATURE:
<223> OTHER INFORMATION: anti-GD2 single-chain antibody

<400> SEQUENCE: 3

Ala Phe Leu Leu Ile Pro Glu Val Lys Leu Val Glu Ser Gly Gly Gly
1               5                   10                  15

Leu Val Leu Pro Gly Asp Ser Leu Arg Leu Ser Cys Ala Thr Ser Glu
            20                  25                  30

Phe Thr Phe Thr Asp Tyr Tyr Met Thr Trp Val Arg Gln Pro Pro Arg
            35                  40                  45

Lys Ala Leu Glu Trp Leu Gly Phe Ile Arg Asn Arg Ala Asn Gly Tyr
50                  55                  60

Thr Thr Glu Tyr Asn Pro Ser Val Lys Gly Arg Phe Thr Ile Ser Arg
65                  70                  75                  80

Asp Asn Ser Gln Ser Ile Leu Tyr Leu Gln Met Asn Thr Leu Arg Thr
                85                  90                  95

Glu Asp Ser Ala Thr Tyr Tyr Cys Ala Arg Val Ser Asn Trp Ala Phe
            100                 105                 110

Asp Tyr Trp Gly Gln Gly Thr Thr Leu Thr Val Ser Ser Gly Ser Thr
            115                 120                 125

Ser Gly Ser Gly Lys Pro Gly Ser Ser Glu Gly Ser Thr Lys Gly Asp
    130                 135                 140

Val Val Met Thr Gln Thr Pro Leu Ser Leu Pro Val Ser Leu Gly Asp
145                 150                 155                 160

Gln Ala Ser Ile Ser Cys Arg Ser Ser Gln Ser Leu Leu Lys Asn Asn
                165                 170                 175

Gly Asn Thr Phe Leu His Trp Tyr Leu Gln Lys Ser Gly Gln Ser Pro
            180                 185                 190

Lys Leu Leu Ile Tyr Lys Val Ser Asn Arg Leu Ser Gly Val Pro Asp
            195                 200                 205

Arg Phe Ser Gly Ser Gly Ser Gly Thr Tyr Phe Thr Leu Lys Ile Ser
    210                 215                 220

Arg Val Glu Ala Glu Asp Leu Gly Val Tyr Phe Cys Ser Gln Ser Thr
225                 230                 235                 240

His Ile Pro Tyr Thr Phe Gly Gly Gly Thr Lys Leu Glu Ile Lys
                245                 250                 255

<210> SEQ ID NO 4
<211> LENGTH: 163
<212> TYPE: PRT
<213> ORGANISM: Artificial sequence
<220> FEATURE:
<223> OTHER INFORMATION: costimulatory signaling domain

<400> SEQUENCE: 4

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Ala Ser Gly Gly Gly
            100                 105                 110

```
Gly Ser Gly Gly Gly Ser Val Val Lys Arg Gly Arg Lys Lys Leu
        115                 120                 125

Leu Tyr Ile Phe Lys Gln Pro Phe Met Arg Pro Val Gln Thr Thr Gln
    130                 135                 140

Glu Glu Asp Gly Cys Ser Cys Arg Phe Pro Glu Glu Glu Glu Gly Gly
145                 150                 155                 160

Cys Glu Leu

<210> SEQ ID NO 5
<211> LENGTH: 39
<212> TYPE: PRT
<213> ORGANISM: Artificial sequence
<220> FEATURE:
<223> OTHER INFORMATION: CD28 extracellular signal

<400> SEQUENCE: 5

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 6
<211> LENGTH: 27
<212> TYPE: PRT
<213> ORGANISM: Artificial sequence
<220> FEATURE:
<223> OTHER INFORMATION: CD28 cell membrane signal

<400> SEQUENCE: 6

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 7
<211> LENGTH: 43
<212> TYPE: PRT
<213> ORGANISM: Artificial sequence
<220> FEATURE:
<223> OTHER INFORMATION: CD28 intracellular signal

<400> SEQUENCE: 7

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Ala Ser
        35                  40

<210> SEQ ID NO 8
<211> LENGTH: 44
<212> TYPE: PRT
<213> ORGANISM: Artificial sequence
<220> FEATURE:
<223> OTHER INFORMATION: 4-1BB intracellular signal

<400> SEQUENCE: 8

Val Val Lys Arg Gly Arg Lys Lys Leu Leu Tyr Ile Phe Lys Gln Pro
1               5                   10                  15

Phe Met Arg Pro Val Gln Thr Thr Gln Glu Glu Asp Gly Cys Ser Cys
```

```
                20                  25                  30
Arg Phe Pro Glu Glu Glu Gly Gly Cys Glu Leu
            35                  40
```

<210> SEQ ID NO 9
<211> LENGTH: 423
<212> TYPE: PRT
<213> ORGANISM: Artificial sequence
<220> FEATURE:
<223> OTHER INFORMATION: caspase 9

<400> SEQUENCE: 9

```
Gly Ser Gly Ala Thr Asn Phe Ser Leu Leu Lys Gln Ala Gly Asp Val
1               5                   10                  15

Glu Glu Asn Pro Gly Pro Met Gly Val Gln Val Glu Thr Ile Ser Pro
            20                  25                  30

Gly Asp Gly Arg Thr Phe Pro Lys Arg Gly Gln Thr Cys Val Val His
        35                  40                  45

Tyr Thr Gly Met Leu Glu Asp Gly Lys Lys Val Asp Ser Ser Arg Asp
50                  55                  60

Arg Asn Lys Pro Phe Lys Phe Met Leu Gly Lys Gln Glu Val Ile Arg
65                  70                  75                  80

Gly Trp Glu Glu Gly Val Ala Gln Met Ser Val Gly Gln Arg Ala Lys
                85                  90                  95

Leu Thr Ile Ser Pro Asp Tyr Ala Tyr Gly Ala Thr Gly His Pro Gly
            100                 105                 110

Ile Ile Pro Pro His Ala Thr Leu Val Phe Asp Val Glu Leu Leu Lys
        115                 120                 125

Leu Glu Gly Gly Gly Ser Gly Gly Gly Ser Gly Ala Met Val
130                 135                 140

Gly Ala Leu Glu Ser Leu Arg Gly Asn Ala Asp Leu Ala Tyr Ile Leu
145                 150                 155                 160

Ser Met Glu Pro Cys Gly His Cys Leu Ile Ile Asn Asn Val Asn Phe
                165                 170                 175

Cys Arg Glu Ser Gly Leu Arg Thr Arg Thr Gly Ser Asn Ile Asp Cys
            180                 185                 190

Glu Lys Leu Arg Arg Arg Phe Ser Ser Leu His Phe Met Val Glu Val
        195                 200                 205

Lys Gly Asp Leu Thr Ala Lys Lys Met Val Leu Ala Leu Leu Glu Leu
210                 215                 220

Ala Arg Gln Asp His Gly Ala Leu Asp Cys Cys Val Val Val Ile Leu
225                 230                 235                 240

Ser His Gly Cys Gln Ala Ser His Leu Gln Phe Pro Gly Ala Val Tyr
                245                 250                 255

Gly Thr Asp Gly Cys Pro Val Ser Val Glu Lys Ile Val Asn Ile Phe
            260                 265                 270

Asn Gly Thr Ser Cys Pro Ser Leu Gly Gly Lys Pro Lys Leu Phe Phe
        275                 280                 285

Ile Gln Ala Cys Gly Gly Glu Gln Lys Asp His Gly Phe Glu Val Ala
290                 295                 300

Ser Thr Ser Pro Glu Asp Glu Ser Pro Gly Ser Asn Pro Glu Pro Asp
305                 310                 315                 320

Ala Thr Pro Phe Gln Glu Gly Leu Arg Thr Phe Asp Gln Leu Asp Ala
                325                 330                 335

Ile Ser Ser Leu Pro Thr Pro Ser Asp Ile Phe Val Ser Tyr Ser Thr
```

```
                    340                 345                 350
Phe Pro Gly Phe Val Ser Trp Arg Asp Pro Lys Ser Gly Ser Trp Tyr
            355                 360                 365

Val Glu Thr Leu Asp Asp Ile Phe Glu Gln Trp Ala His Ser Glu Asp
370                 375                 380

Leu Gln Ser Leu Leu Arg Val Ala Asn Ala Val Ser Val Lys Gly
385                 390                 395                 400

Ile Tyr Lys Gln Met Pro Gly Cys Phe Asn Phe Leu Arg Lys Lys Leu
            405                 410                 415

Phe Phe Lys Thr Ser Ala Ser
            420

<210> SEQ ID NO 10
<211> LENGTH: 22
<212> TYPE: PRT
<213> ORGANISM: Artificial sequence
<220> FEATURE:
<223> OTHER INFORMATION: Secretory signal peptide

<400> SEQUENCE: 10

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 11
<211> LENGTH: 21
<212> TYPE: PRT
<213> ORGANISM: Artificial sequence
<220> FEATURE:
<223> OTHER INFORMATION: Secretory signal peptide

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 981
<212> TYPE: PRT
<213> ORGANISM: Artificial sequence
<220> FEATURE:
<223> OTHER INFORMATION: chimeric antigen receptor

<400> SEQUENCE: 12

Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Pro Gly
            20                  25                  30

Val Val Gln Pro Gly Arg Ser Leu Arg Ile Ser Cys Ala Val Ser Gly
        35                  40                  45

Phe Ser Val Thr Asn Tyr Gly Val His Trp Val Arg Gln Pro Pro Gly
    50                  55                  60

Lys Gly Leu Glu Trp Leu Gly Val Ile Trp Ala Gly Gly Ile Thr Asn
65                  70                  75                  80

Tyr Asn Ser Ala Phe Met Ser Arg Leu Thr Ile Ser Lys Asp Asn Ser
                85                  90                  95

Lys Asn Thr Val Tyr Leu Gln Met Asn Ser Leu Arg Ala Glu Asp Thr
            100                 105                 110
```

```
Ala Met Tyr Tyr Cys Ala Ser Arg Gly Gly His Tyr Gly Tyr Ala Leu
            115                 120                 125

Asp Tyr Trp Gly Gln Gly Thr Leu Val Thr Val Ser Ser Gly Ser Thr
    130                 135                 140

Ser Gly Ser Gly Lys Pro Gly Ser Ser Glu Gly Ser Thr Lys Gly Glu
145                 150                 155                 160

Ile Val Met Thr Gln Thr Pro Ala Thr Leu Ser Val Ser Ala Gly Glu
                165                 170                 175

Arg Val Thr Ile Thr Cys Lys Ala Ser Gln Ser Val Ser Asn Asp Val
            180                 185                 190

Thr Trp Tyr Gln Gln Lys Pro Gly Gln Ala Pro Arg Leu Leu Ile Tyr
    195                 200                 205

Ser Ala Ser Asn Arg Tyr Ser Gly Val Pro Ala Arg Phe Ser Gly Ser
210                 215                 220

Gly Tyr Gly Thr Glu Phe Thr Phe Thr Ile Ser Ser Val Gln Ser Glu
225                 230                 235                 240

Asp Phe Ala Val Tyr Phe Cys Gln Gln Asp Tyr Ser Ser Phe Gly Gln
                245                 250                 255

Gly Thr Lys Leu Glu Ile Lys Ala Ala Ala Ile Glu Val Met Tyr Pro
            260                 265                 270

Pro Pro Tyr Leu Asp Asn Glu Lys Ser Asn Gly Thr Ile Ile His Val
    275                 280                 285

Lys Gly Lys His Leu Cys Pro Ser Pro Leu Phe Pro Gly Pro Ser Lys
290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
    355                 360                 365

Ala Ala Tyr Arg Ser Ala Ser Gly Gly Gly Ser Gly Gly Gly Gly
370                 375                 380

Ser Val Val Lys Arg Gly Arg Lys Lys Leu Leu Tyr Ile Phe Lys Gln
385                 390                 395                 400

Pro Phe Met Arg Pro Val Gln Thr Thr Gln Glu Glu Asp Gly Cys Ser
                405                 410                 415

Cys Arg Phe Pro Glu Glu Glu Glu Gly Gly Cys Glu Leu Gly Gly Gly
            420                 425                 430

Gly Ser Gly Gly Gly Gly Ser Gly Gly Gly Gly Ser Arg Val Lys Phe
    435                 440                 445

Ser Arg Ser Ala Asp Ala Pro Ala Tyr Gln Gln Gly Gln Asn Gln Leu
450                 455                 460

Tyr Asn Glu Leu Asn Leu Gly Arg Arg Glu Glu Tyr Asp Val Leu Asp
465                 470                 475                 480

Lys Arg Arg Gly Arg Asp Pro Glu Met Gly Gly Lys Pro Arg Arg Lys
                485                 490                 495

Asn Pro Gln Glu Gly Leu Tyr Asn Glu Leu Gln Lys Asp Lys Met Ala
            500                 505                 510

Glu Ala Tyr Ser Glu Ile Gly Met Lys Gly Glu Arg Arg Gly Lys
    515                 520                 525
```

-continued

```
Gly His Asp Gly Leu Tyr Gln Gly Leu Ser Thr Ala Thr Lys Asp Thr
        530                 535                 540

Tyr Asp Ala Leu His Met Gln Ala Leu Pro Pro Arg Thr Ser Gly Ser
545                 550                 555                 560

Gly Ala Thr Asn Phe Ser Leu Leu Lys Gln Ala Gly Asp Val Glu Glu
                565                 570                 575

Asn Pro Gly Pro Met Gly Val Gln Val Glu Thr Ile Ser Pro Gly Asp
            580                 585                 590

Gly Arg Thr Phe Pro Lys Arg Gly Gln Thr Cys Val Val His Tyr Thr
        595                 600                 605

Gly Met Leu Glu Asp Gly Lys Lys Val Asp Ser Ser Arg Asp Arg Asn
    610                 615                 620

Lys Pro Phe Lys Phe Met Leu Gly Lys Gln Glu Val Ile Arg Gly Trp
625                 630                 635                 640

Glu Glu Gly Val Ala Gln Met Ser Val Gly Gln Arg Ala Lys Leu Thr
                645                 650                 655

Ile Ser Pro Asp Tyr Ala Tyr Gly Ala Thr Gly His Pro Gly Ile Ile
            660                 665                 670

Pro Pro His Ala Thr Leu Val Phe Asp Val Glu Leu Leu Lys Leu Glu
        675                 680                 685

Gly Gly Gly Gly Ser Gly Gly Gly Ser Gly Ala Met Val Gly Ala
    690                 695                 700

Leu Glu Ser Leu Arg Gly Asn Ala Asp Leu Ala Tyr Ile Leu Ser Met
705                 710                 715                 720

Glu Pro Cys Gly His Cys Leu Ile Ile Asn Asn Val Asn Phe Cys Arg
                725                 730                 735

Glu Ser Gly Leu Arg Thr Arg Thr Gly Ser Asn Ile Asp Cys Glu Lys
            740                 745                 750

Leu Arg Arg Arg Phe Ser Ser Leu His Phe Met Val Glu Val Lys Gly
        755                 760                 765

Asp Leu Thr Ala Lys Lys Met Val Leu Ala Leu Leu Glu Leu Ala Arg
    770                 775                 780

Gln Asp His Gly Ala Leu Asp Cys Cys Val Val Val Ile Leu Ser His
785                 790                 795                 800

Gly Cys Gln Ala Ser His Leu Gln Phe Pro Gly Ala Val Tyr Gly Thr
                805                 810                 815

Asp Gly Cys Pro Val Ser Val Glu Lys Ile Val Asn Ile Phe Asn Gly
            820                 825                 830

Thr Ser Cys Pro Ser Leu Gly Gly Lys Pro Lys Leu Phe Phe Ile Gln
        835                 840                 845

Ala Cys Gly Gly Glu Gln Lys Asp His Gly Phe Glu Val Ala Ser Thr
    850                 855                 860

Ser Pro Glu Asp Glu Ser Pro Gly Ser Asn Pro Glu Pro Asp Ala Thr
865                 870                 875                 880

Pro Phe Gln Glu Gly Leu Arg Thr Phe Asp Gln Leu Asp Ala Ile Ser
                885                 890                 895

Ser Leu Pro Thr Pro Ser Asp Ile Phe Val Ser Tyr Ser Thr Phe Pro
            900                 905                 910

Gly Phe Val Ser Trp Arg Asp Pro Lys Ser Gly Ser Trp Tyr Val Glu
        915                 920                 925

Thr Leu Asp Asp Ile Phe Glu Gln Trp Ala His Ser Glu Asp Leu Gln
    930                 935                 940

Ser Leu Leu Leu Arg Val Ala Asn Ala Val Ser Val Lys Gly Ile Tyr
```

```
            945                 950                 955                 960
Lys Gln Met Pro Gly Cys Phe Asn Phe Leu Arg Lys Lys Leu Phe Phe
                    965                 970                 975

Lys Thr Ser Ala Ser
            980

<210> SEQ ID NO 13
<211> LENGTH: 976
<212> TYPE: PRT
<213> ORGANISM: Artificial sequence
<220> FEATURE:
<223> OTHER INFORMATION: chimeric antigen receptor

<400> SEQUENCE: 13

Met Leu Leu Leu Val Thr Ser Leu Leu Leu Cys Glu Leu Pro Glu Val
1               5                   10                  15

Gln Leu Val Gln Ser Gly Ala Glu Val Glu Lys Pro Gly Ala Ser Val
            20                  25                  30

Lys Ile Ser Cys Lys Ala Ser Gly Ser Ser Phe Thr Gly Tyr Asn Met
        35                  40                  45

Asn Trp Val Arg Gln Asn Ile Gly Lys Ser Leu Glu Trp Ile Gly Ala
    50                  55                  60

Ile Asp Pro Tyr Tyr Gly Gly Thr Ser Tyr Asn Gln Lys Phe Lys Gly
65                  70                  75                  80

Arg Ala Thr Leu Thr Val Asp Lys Ser Thr Ser Thr Ala Tyr Met His
                85                  90                  95

Leu Lys Ser Leu Arg Ser Glu Asp Thr Ala Val Tyr Tyr Cys Val Ser
            100                 105                 110

Gly Met Glu Tyr Trp Gly Gln Gly Thr Ser Val Thr Val Ser Ser Gly
        115                 120                 125

Ser Thr Ser Gly Ser Gly Lys Pro Gly Ser Ser Glu Gly Ser Thr Lys
    130                 135                 140

Gly Asp Val Val Met Thr Gln Thr Pro Leu Ser Leu Pro Val Thr Pro
145                 150                 155                 160

Gly Glu Pro Ala Ser Ile Ser Cys Arg Ser Ser Gln Ser Leu Val His
                165                 170                 175

Arg Asn Gly Asn Thr Tyr Leu His Trp Tyr Leu Gln Lys Pro Gly Gln
            180                 185                 190

Ser Pro Lys Leu Leu Ile His Lys Val Ser Asn Arg Phe Ser Gly Val
        195                 200                 205

Pro Asp Arg Phe Ser Gly Ser Gly Ser Gly Thr Asp Phe Thr Leu Lys
    210                 215                 220

Ile Ser Arg Val Glu Ala Glu Asp Leu Gly Val Tyr Phe Cys Ser Gln
225                 230                 235                 240

Ser Thr His Val Pro Pro Leu Thr Phe Gly Ala Gly Thr Lys Leu Glu
                245                 250                 255

Leu Lys Ala Ala Ala Ile Glu Val Met Tyr Pro Pro Pro Tyr Leu Asp
            260                 265                 270

Asn Glu Lys Ser Asn Gly Thr Ile Ile His Val Lys Gly Lys His Leu
        275                 280                 285

Cys Pro Ser Pro Leu Phe Pro Gly Pro Ser Lys Pro Phe Trp Val Leu
    290                 295                 300

Val Val Val Gly Gly Val Leu Ala Cys Tyr Ser Leu Leu Val Thr Val
305                 310                 315                 320

Ala Phe Ile Ile Phe Trp Val Arg Ser Lys Arg Ser Arg Leu Leu His
```

```
              325                 330                 335
Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
            355                 360                 365

Ala Ser Gly Gly Gly Gly Ser Gly Gly Gly Gly Ser Val Val Lys Arg
            370                 375                 380

Gly Arg Lys Lys Leu Leu Tyr Ile Phe Lys Gln Pro Phe Met Arg Pro
385                 390                 395                 400

Val Gln Thr Thr Gln Glu Glu Asp Gly Cys Ser Cys Arg Phe Pro Glu
                405                 410                 415

Glu Glu Glu Gly Gly Cys Glu Leu Gly Gly Gly Ser Gly Gly Gly
                420                 425                 430

Gly Ser Gly Gly Gly Gly Ser Arg Val Lys Phe Ser Arg Ser Ala Asp
                435                 440                 445

Ala Pro Ala Tyr Gln Gln Gly Gln Asn Gln Leu Tyr Asn Glu Leu Asn
            450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu
                500                 505                 510

Ile Gly Met Lys Gly Glu Arg Arg Arg Gly Lys Gly His Asp Gly Leu
                515                 520                 525

Tyr Gln Gly Leu Ser Thr Ala Thr Lys Asp Thr Tyr Asp Ala Leu His
            530                 535                 540

Met Gln Ala Leu Pro Pro Arg Thr Ser Gly Ser Gly Ala Thr Asn Phe
545                 550                 555                 560

Ser Leu Leu Lys Gln Ala Gly Asp Val Glu Glu Asn Pro Gly Pro Met
                565                 570                 575

Gly Val Gln Val Glu Thr Ile Ser Pro Gly Asp Gly Arg Thr Phe Pro
                580                 585                 590

Lys Arg Gly Gln Thr Cys Val Val His Tyr Thr Gly Met Leu Glu Asp
                595                 600                 605

Gly Lys Lys Val Asp Ser Ser Arg Asp Arg Asn Lys Pro Phe Lys Phe
            610                 615                 620

Met Leu Gly Lys Gln Glu Val Ile Arg Gly Trp Glu Glu Gly Val Ala
625                 630                 635                 640

Gln Met Ser Val Gly Gln Arg Ala Lys Leu Thr Ile Ser Pro Asp Tyr
                645                 650                 655

Ala Tyr Gly Ala Thr Gly His Pro Gly Ile Ile Pro Pro His Ala Thr
                660                 665                 670

Leu Val Phe Asp Val Glu Leu Leu Lys Leu Glu Gly Gly Gly Ser
                675                 680                 685

Gly Gly Gly Gly Ser Gly Ala Met Val Gly Ala Leu Glu Ser Leu Arg
            690                 695                 700

Gly Asn Ala Asp Leu Ala Tyr Ile Leu Ser Met Glu Pro Cys Gly His
705                 710                 715                 720

Cys Leu Ile Ile Asn Asn Val Asn Phe Cys Arg Glu Ser Gly Leu Arg
                725                 730                 735

Thr Arg Thr Gly Ser Asn Ile Asp Cys Glu Lys Leu Arg Arg Arg Phe
            740                 745                 750
```

```
Ser Ser Leu His Phe Met Val Glu Val Lys Gly Asp Leu Thr Ala Lys
        755                 760                 765

Lys Met Val Leu Ala Leu Leu Glu Leu Ala Arg Gln Asp His Gly Ala
        770                 775                 780

Leu Asp Cys Cys Val Val Val Ile Leu Ser His Gly Cys Gln Ala Ser
785                 790                 795                 800

His Leu Gln Phe Pro Gly Ala Val Tyr Gly Thr Asp Gly Cys Pro Val
                805                 810                 815

Ser Val Glu Lys Ile Val Asn Ile Phe Asn Gly Thr Ser Cys Pro Ser
            820                 825                 830

Leu Gly Gly Lys Pro Lys Leu Phe Phe Ile Gln Ala Cys Gly Gly Glu
                835                 840                 845

Gln Lys Asp His Gly Phe Glu Val Ala Ser Thr Ser Pro Glu Asp Glu
        850                 855                 860

Ser Pro Gly Ser Asn Pro Glu Pro Asp Ala Thr Pro Phe Gln Glu Gly
865                 870                 875                 880

Leu Arg Thr Phe Asp Gln Leu Asp Ala Ile Ser Ser Leu Pro Thr Pro
                885                 890                 895

Ser Asp Ile Phe Val Ser Tyr Ser Thr Phe Pro Gly Phe Val Ser Trp
            900                 905                 910

Arg Asp Pro Lys Ser Gly Ser Trp Tyr Val Glu Thr Leu Asp Asp Ile
                915                 920                 925

Phe Glu Gln Trp Ala His Ser Glu Asp Leu Gln Ser Leu Leu Leu Arg
        930                 935                 940

Val Ala Asn Ala Val Ser Val Lys Gly Ile Tyr Lys Gln Met Pro Gly
945                 950                 955                 960

Cys Phe Asn Phe Leu Arg Lys Lys Leu Phe Phe Lys Thr Ser Ala Ser
                965                 970                 975

<210> SEQ ID NO 14
<211> LENGTH: 987
<212> TYPE: PRT
<213> ORGANISM: Artificial sequence
<220> FEATURE:
<223> OTHER INFORMATION: chimeric antigen receptor

<400> SEQUENCE: 14

Met Leu Leu Leu Val Thr Ser Leu Leu Cys Glu Leu Pro Ala Phe
1               5                   10                  15

Leu Leu Ile Pro Glu Val Lys Leu Val Glu Ser Gly Gly Gly Leu Val
            20                  25                  30

Leu Pro Gly Asp Ser Leu Arg Leu Ser Cys Ala Thr Ser Glu Phe Thr
        35                  40                  45

Phe Thr Asp Tyr Tyr Met Thr Trp Val Arg Gln Pro Pro Arg Lys Ala
    50                  55                  60

Leu Glu Trp Leu Gly Phe Ile Arg Asn Arg Ala Asn Gly Tyr Thr Thr
65                  70                  75                  80

Glu Tyr Asn Pro Ser Val Lys Gly Arg Phe Thr Ile Ser Arg Asp Asn
                85                  90                  95

Ser Gln Ser Ile Leu Tyr Leu Gln Met Asn Thr Leu Arg Thr Glu Asp
            100                 105                 110

Ser Ala Thr Tyr Tyr Cys Ala Arg Val Ser Asn Trp Ala Phe Asp Tyr
        115                 120                 125

Trp Gly Gln Gly Thr Thr Leu Thr Val Ser Ser Gly Ser Thr Ser Gly
    130                 135                 140
```

```
Ser Gly Lys Pro Gly Ser Ser Glu Gly Ser Thr Lys Gly Asp Val Val
145                 150                 155                 160

Met Thr Gln Thr Pro Leu Ser Leu Pro Val Ser Leu Gly Asp Gln Ala
            165                 170                 175

Ser Ile Ser Cys Arg Ser Ser Gln Ser Leu Leu Lys Asn Asn Gly Asn
        180                 185                 190

Thr Phe Leu His Trp Tyr Leu Gln Lys Ser Gly Gln Ser Pro Lys Leu
    195                 200                 205

Leu Ile Tyr Lys Val Ser Asn Arg Leu Ser Gly Val Pro Asp Arg Phe
210                 215                 220

Ser Gly Ser Gly Ser Gly Thr Tyr Phe Thr Leu Lys Ile Ser Arg Val
225                 230                 235                 240

Glu Ala Glu Asp Leu Gly Val Tyr Phe Cys Ser Gln Ser Thr His Ile
                245                 250                 255

Pro Tyr Thr Phe Gly Gly Gly Thr Lys Leu Glu Ile Lys Ala Ala Ala
            260                 265                 270

Ile Glu Val Met Tyr Pro Pro Tyr Leu Asp Asn Glu Lys Ser Asn
        275                 280                 285

Gly Thr Ile Ile His Val Lys Gly Lys His Leu Cys Pro Ser Pro Leu
    290                 295                 300

Phe Pro Gly Pro Ser Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
            355                 360                 365

Ala Pro Pro Arg Asp Phe Ala Ala Tyr Arg Ser Ala Ser Gly Gly Gly
            370                 375                 380

Gly Ser Gly Gly Gly Gly Ser Val Val Lys Arg Gly Arg Lys Lys Leu
385                 390                 395                 400

Leu Tyr Ile Phe Lys Gln Pro Phe Met Arg Pro Val Gln Thr Thr Gln
                405                 410                 415

Glu Glu Asp Gly Cys Ser Cys Arg Phe Pro Glu Glu Glu Glu Gly Gly
            420                 425                 430

Cys Glu Leu Gly Gly Gly Ser Gly Gly Gly Ser Gly Gly Gly
            435                 440                 445

Gly Ser Arg Val Lys Phe Ser Arg Ser Ala Asp Ala Pro Ala Tyr Gln
            450                 455                 460

Gln Gly Gln Asn Gln Leu Tyr Asn Glu Leu Asn Leu Gly Arg Arg Glu
465                 470                 475                 480

Glu Tyr Asp Val Leu Asp Lys Arg Arg Gly Arg Asp Pro Glu Met Gly
                485                 490                 495

Gly Lys Pro Arg Arg Lys Asn Pro Gln Glu Gly Leu Tyr Asn Glu Leu
            500                 505                 510

Gln Lys Asp Lys Met Ala Glu Ala Tyr Ser Glu Ile Gly Met Lys Gly
            515                 520                 525

Glu Arg Arg Arg Gly Lys Gly His Asp Gly Leu Tyr Gln Gly Leu Ser
            530                 535                 540

Thr Ala Thr Lys Asp Thr Tyr Asp Ala Leu His Met Gln Ala Leu Pro
545                 550                 555                 560
```

-continued

```
Pro Arg Thr Ser Gly Ser Gly Ala Thr Asn Phe Ser Leu Leu Lys Gln
            565                 570                 575

Ala Gly Asp Val Glu Glu Asn Pro Gly Pro Met Gly Val Gln Val Glu
        580                 585                 590

Thr Ile Ser Pro Gly Asp Gly Arg Thr Phe Pro Lys Arg Gly Gln Thr
    595                 600                 605

Cys Val Val His Tyr Thr Gly Met Leu Glu Asp Gly Lys Lys Val Asp
    610                 615                 620

Ser Ser Arg Asp Arg Asn Lys Pro Phe Lys Phe Met Leu Gly Lys Gln
625                 630                 635                 640

Glu Val Ile Arg Gly Trp Glu Glu Gly Val Ala Gln Met Ser Val Gly
            645                 650                 655

Gln Arg Ala Lys Leu Thr Ile Ser Pro Asp Tyr Ala Tyr Gly Ala Thr
            660                 665                 670

Gly His Pro Gly Ile Ile Pro Pro His Ala Thr Leu Val Phe Asp Val
        675                 680                 685

Glu Leu Leu Lys Leu Glu Gly Gly Gly Ser Gly Gly Gly Gly Ser
    690                 695                 700

Gly Ala Met Val Gly Ala Leu Glu Ser Leu Arg Gly Asn Ala Asp Leu
705                 710                 715                 720

Ala Tyr Ile Leu Ser Met Glu Pro Cys Gly His Cys Leu Ile Ile Asn
            725                 730                 735

Asn Val Asn Phe Cys Arg Glu Ser Gly Leu Arg Thr Arg Thr Gly Ser
            740                 745                 750

Asn Ile Asp Cys Glu Lys Leu Arg Arg Arg Phe Ser Ser Leu His Phe
        755                 760                 765

Met Val Glu Val Lys Gly Asp Leu Thr Ala Lys Lys Met Val Leu Ala
    770                 775                 780

Leu Leu Glu Leu Ala Arg Gln Asp His Gly Ala Leu Asp Cys Cys Val
785                 790                 795                 800

Val Val Ile Leu Ser His Gly Cys Gln Ala Ser His Leu Gln Phe Pro
            805                 810                 815

Gly Ala Val Tyr Gly Thr Asp Gly Cys Pro Val Ser Val Glu Lys Ile
            820                 825                 830

Val Asn Ile Phe Asn Gly Thr Ser Cys Pro Ser Leu Gly Gly Lys Pro
        835                 840                 845

Lys Leu Phe Phe Ile Gln Ala Cys Gly Gly Glu Gln Lys Asp His Gly
    850                 855                 860

Phe Glu Val Ala Ser Thr Ser Pro Glu Asp Glu Ser Pro Gly Ser Asn
865                 870                 875                 880

Pro Glu Pro Asp Ala Thr Pro Phe Gln Glu Gly Leu Arg Thr Phe Asp
            885                 890                 895

Gln Leu Asp Ala Ile Ser Ser Leu Pro Thr Pro Ser Asp Ile Phe Val
            900                 905                 910

Ser Tyr Ser Thr Phe Pro Gly Phe Val Ser Trp Arg Asp Pro Lys Ser
        915                 920                 925

Gly Ser Trp Tyr Val Glu Thr Leu Asp Asp Ile Phe Glu Gln Trp Ala
    930                 935                 940

His Ser Glu Asp Leu Gln Ser Leu Leu Leu Arg Val Ala Asn Ala Val
945                 950                 955                 960
```

-continued

```
Ser Val Lys Gly Ile Tyr Lys Gln Met Pro Gly Cys Phe Asn Phe Leu
                965                 970                 975

Arg Lys Lys Leu Phe Phe Lys Thr Ser Ala Ser
            980                 985
```